United States Patent
Cree et al.

(10) Patent No.: US 6,942,748 B2
(45) Date of Patent: Sep. 13, 2005

(54) TEAR RESISTANT ELASTIC LAMINATE AND METHOD OF FORMING

(75) Inventors: James W. Cree, Mundeelein, IL (US); Jeffrey A. Middlesworth, Wauconda, IL (US); Stephen D. Bruce, Crystal Lake, IL (US)

(73) Assignee: Tredegar Film Products Corporation, Richmond, VA (US)

( * ) Notice: Subject to any disclaimer, the term of this patent is extended or adjusted under 35 U.S.C. 154(b) by 277 days.

(21) Appl. No.: 10/234,081

(22) Filed: Aug. 30, 2002

(65) Prior Publication Data

US 2003/0022582 A1 Jan. 30, 2003

Related U.S. Application Data

(62) Division of application No. 09/491,721, filed on Jan. 27, 2000.
(60) Provisional application No. 60/151,472, filed on Aug. 30, 1999.

(51) Int. Cl.[7] .......................... B32B 5/26; B32B 27/12; B32B 3/10
(52) U.S. Cl. ...................... 156/229; 156/73.1; 156/160; 156/163; 156/182; 156/290; 428/141; 442/407; 442/394
(58) Field of Search ........................................ 156/229

(56) References Cited

U.S. PATENT DOCUMENTS

| | | |
|---|---|---|
| 4,525,407 A | 6/1985 | Ness |
| 4,804,378 A | 2/1989 | Shiba et al. |
| 4,857,067 A | 8/1989 | Wood et al. |
| 4,863,779 A * | 9/1989 | Daponte ..................... 428/152 |
| 4,981,747 A | 1/1991 | Morman |
| 5,226,992 A | 7/1993 | Morman |
| 5,335,908 A | 8/1994 | Bamber |
| 5,336,545 A | 8/1994 | Morman |
| 5,354,597 A | 10/1994 | Capik et al. |
| 5,385,775 A * | 1/1995 | Wright ....................... 442/183 |
| 5,399,895 A | 3/1995 | Koga |
| 5,422,172 A | 6/1995 | Wu |
| 5,496,429 A | 3/1996 | Hasse et al. |
| 5,514,470 A * | 5/1996 | Haffner et al. .............. 428/343 |
| 5,543,206 A | 8/1996 | Austin et al. |
| 5,580,411 A | 12/1996 | Nease et al. |
| 5,624,424 A * | 4/1997 | Saisaka et al. ......... 604/385.28 |
| 5,628,741 A | 5/1997 | Buell et al. |
| H1674 H | 8/1997 | Ames et al. |
| 5,669,897 A | 9/1997 | Lavon et al. |
| 5,683,533 A | 11/1997 | Keighley et al. |
| 5,700,255 A | 12/1997 | Curro et al. |
| 5,705,913 A | 1/1998 | Takeuchi et al. |
| 5,709,921 A | 1/1998 | Shawver |
| 5,789,065 A | 8/1998 | Haffner et al. |
| 5,804,286 A * | 9/1998 | Quantrille et al. .......... 428/198 |

(Continued)

FOREIGN PATENT DOCUMENTS

| | | | | |
|---|---|---|---|---|
| WO | WO 9616122 A1 * | 5/1996 | ........... | C08L/53/02 |
| WO | WO 200153076 A1 * | 7/2001 | ........... | A61F/13/15 |

*Primary Examiner*—Sue A. Purvis
(74) *Attorney, Agent, or Firm*—Joseph A. Tessari; Joseph E. Chovanes

(57) ABSTRACT

An elastomeric film is bonded between two or more layers of nonwoven webs formed of nonelastomeric thermoplastic fibers. The laminate has, in a predefined transverse direction, an elastic elongation value greater than the predefined elastic elongation value of the nonwoven webs, and an ultimate force to break in the predefined transverse direction of at least 3000 g/in. The laminate advantageously provides a tear resistant, multiple ply, fabric that is soft to the touch as a result of the outwardly disposed nonwoven webs, and has a high elastic modulus. The laminate is particularly useful in applications where closure portions of a product must be stretched to keep the product in place when worn.

7 Claims, 2 Drawing Sheets

U.S. PATENT DOCUMENTS

| | | |
|---|---|---|
| 5,817,400 A | 10/1998 | Chen et al. |
| 5,841,074 A | 11/1998 | Egan et al. |
| 5,843,057 A | 12/1998 | McCormack |
| 5,846,232 A | 12/1998 | Serbiak et al. |
| 5,857,881 A | 1/1999 | Zippel, Sr. |
| 5,904,710 A | 5/1999 | Davis et al. |
| 5,906,637 A | 5/1999 | Davis et al. |
| 5,932,497 A * | 8/1999 | Morman et al. ............ 442/286 |
| 6,001,460 A | 12/1999 | Morman et al. |
| 6,096,668 A | 8/2000 | Abuto et al. |
| 6,726,983 B2 * | 4/2004 | Erdos et al. ............. 428/195.1 |
| 2002/0002021 A1 * | 1/2002 | May et al. .................. 442/381 |
| 2003/0017345 A1 * | 1/2003 | Middlesworth et al. 156/244.11 |
| 2003/0084986 A1 * | 5/2003 | Cree et al. .................. 156/229 |

* cited by examiner

TEAR RESISTANT ELASTIC LAMINATE AND METHOD OF FORMING

CROSS-REFERENCE TO RELATED APPLICATIONS

This Application is a divisional of U.S. application Ser. No. 09/491,721, filed Jan. 27, 2000.

This application claims the benefit under Title 35 United States Code §119(e) of U.S. Provisional Application No. 60/151,472, filed Aug. 30, 1999.

BACKGROUND OF THE INVENTION

1. Technical Field

This invention relates generally to elastic laminates, and more particularly to a laminate having an elastic polymer film core with at least one layer of an extensible nonwoven web bonded to each side of the elastic polymer film core.

2. Background Art

There is a recognized need for a tear resistant elastic laminate that has a soft, comfortable outer surface. For example, in personal hygiene products such as diapers, there is a need for an elastic ear that can be stretched to provide a comfortable fit for the different anatomies of various wearers, improve the fit and comfort, reduce leakage, and be compatible with adhesive and mechanical fasteners. To provide the necessary stretching characteristics, the diaper ear must be formed of an elastic material that can stretch and recover without tearing prematurely. Moreover, there is a need to provide a lightweight cloth-like film based laminate that has an elastic recovery from stretching that is comparable to natural or synthetic rubber films in the transverse direction, and has a tear resistance that is comparable to durable cotton or fabrics composed of LYRCA® synthetic fibers or filaments.

Several arrangements have been proposed for tear-resistant elastic laminates. For example, U.S. Pat. No. 5,709,921 issued Jan. 20, 1998 to Susan Elaine Shawver, discloses a multi-layer material formed of layers of elastomeric films, fibers, or webs. However, elastomeric materials, when disposed as the outer surface of a laminate, do not provide the softness and comfort characteristics of nonelastomeric outer webs. U.S. Pat. No. 5,226,992 issued Jul. 13, 1993 to Michael T. Morman, requires the use of force to pre-tension a necked non-woven prior to laminating to form a composite elastic neck-bonded laminate. This laminate is stretchable in a direction parallel to the direction of constriction or necking. It does not provide strong tear resistance due to the presence of the stressed necked material layer in the laminate. Another patent, also issued to Michael T. Morman, U.S. Pat. No. 4,981,474 on Jan. 1, 1991, discloses a composite material having a nonelastic material bonded to an elastic material while the elastic material is in a stretched condition so that when the elastic material is relaxed, the nonelastic material gathers between the locations where it is bonded to the elastic material. The resulting composite elastic material is only stretchable to the extent that the nonelastic material gathered between the bond locations allows the elastic material to elongate. Thus, in this arrangement, the elasticity of the laminate is limited by the inability of the nonelastic material to stretch beyond its initial dimensions. Moreover, the formed laminate is bulky and difficult to process. Another example of an elastic laminated sheet is disclosed in U.S. Pat. No. 5,422,172 issued Jun. 6, 1995 to Pai-Chuan Wu, which discloses an elastic laminate formed by stretching, thus compromising the tear resistance of the laminate. U.S. Pat. No. 5,354,597 issued Oct. 11, 1994 to Karen M. Capik, et al, discloses an adhesive tape having a multi-layered construction in which at least one of the layers is formed of an elastomeric material and at least one other layer that is pre-stretched beyond its elastic limit. The tape does not provide the softness or comfort provided by an externally disposed nonwoven web.

The present invention is directed to overcoming the problems set forth above. There is a demonstrated need for a laminate that has the outer softness of a nonelastomeric nonwoven web, the elasticity of an elastomeric film, and the tear resistance of a conventional packaging film. There is also a demonstrated need for such a laminate that is easy to form and economical to produce.

SUMMARY OF THE INVENTION

In accordance with one aspect of the present invention, a tear resistant laminate comprises an elastic polymeric film that has a first nonwoven web formed of nonelastic fibers bonded to a top surface of the elastic polymeric film and a second nonwoven web formed of nonelastic fibers bonded to a bottom surface of the elastic polymeric film. Each of the nonwoven webs has a permanent deformation range from about 20% to about 200%, measured in a predefined transverse direction, and an ultimate force to break of greater than 1,500 g/in. in said predefined transverse direction. The laminate has an elastic elongation value greater than the elastic elongation values of the first and second nonwoven webs, and an ultimate force to break value of at least 3,000 g/in.

Other features of the tear resistant laminate embodying the present invention include the first and second nonwoven webs being formed of randomly disposed nonelastomeric thermoplastic fibers, with at least about 10% of the fibers having approximately equal softening temperatures. Other features include from about 2% to about 50% of the nonelastomeric thermoplastic fibers being disposed in a skewed direction at an angle greater than about 10 degrees from a predefined machine direction of the respective nonwoven web. Still other features include the nonelastomeric thermoplastic fibers comprising the first and second nonwoven webs having a mass divided by length value of at least about 1.5 denier. Yet additional features include the nonelastomeric thermoplastic fibers being formed of a polyolefin fiber. Desirably, the polyolefin nonwoven web has a basis weight of from about 14 g/m$^2$ to about 60 g/m$^2$.

Still additional features of the tear-resistant laminate embodying the present invention include the elastic polymeric film being a metallocene-catalyzed low-density polyethylene film. Yet other features include the metallocene-catalyzed low-density polyethylene film having a basis weight of from about 18 g/m$^2$ to about 100 g/m$^2$. Another feature includes the elastic polymeric film having stretch to break properties greater than the stretch to break values of the nonwoven webs. Additional features include the elastic polymeric film being formed of a copolymer blend, for example a block-copolymer blend, a thermoplastic urethane, or a cross-linked rubber film having a basis weight of from about 30 g/m$^2$ to about 100 g/m$^2$. Important additional features include the elastic polymeric film being a perforated film.

Yet additional features of the tear-resistant laminate embodying the present invention include the bond between the respective first and second nonwoven webs and the top and bottom surfaces of the polymeric film being a mutually bonded surface area between the respective web surfaces and the film surfaces of at least 3.0% of the respective total surface areas. Still additional features include the first and second nonwoven webs each being separate, multi-layered composite structures formed of two or more layers of nonwoven fabric bonded together.

In accordance with another aspect of the present invention, a method for forming a tear-resistant laminate includes selecting an elastic polymeric film having a basis weight of from about 18 g/m² to about 100 g/m², selecting a first nonwoven web formed of randomly disposed non-elastomeric thermoplastic fibers, heating the first nonwoven web at a temperature between the softening temperature and the melting temperature of at least 10% of the thermoplastic fibers, drawing the heated first nonwoven web under tension in a substantially longitudinal direction, and cooling the first nonwoven web whereby the first nonwoven web is consolidated laterally and is extensible in a direction transverse to the longitudinal direction. Further steps include selecting a second nonwoven web formed of randomly disposed non-elastomeric thermoplastic fibers, heating the second nonwoven web to a temperature between the softening temperature and the melting temperatures of at least about 10% of the thermoplastic fibers, drawing the heated second nonwoven web under tension in a substantially longitudinal direction to cause the web to be longitudinally elongated, and cooling the second nonwoven web whereby the second nonwoven web is consolidated laterally and is extensible in a direction transverse to the longitudinal direction. The bottom surface of the first nonwoven web is then bonded to the top surface of the elastomeric film and the top surface of the second nonwoven web is bonded to the bottom surface of the elastomeric film by thermal fusion with the addition of an applied pressure to produce mutually bonded surface areas between the respective nonwoven web surfaces and the elastomeric film surfaces of at least 3% of the respective total mutually opposed surface areas.

Other features include the step of bonding the respective nonwoven webs with the elastomeric film being carried out by ultrasonic welding.

Other features of the method of forming a tear-resistant laminate, in accordance with the present invention, include forming the first and second nonwoven webs of two or more separately preformed layers of nonwoven material.

BRIEF DESCRIPTION OF THE DRAWINGS

A more complete understanding of the structure and operation of the present invention may be had by reference to the following detailed description when taken in conjunction with the accompanying drawings, wherein.

DETAILED DESCRIPTION OF PRESENTLY PREFERRED EXEMPLARY EMBODIMENTS

The term "nonwoven web" as used herein means a fabric formed of randomly laid fibers or filaments to form a web wherein some of the fibers are bonded by fiber-to-fiber fusion, by fiber entanglement, or by thermal bonds such as point bonding.

The term "machine direction", as used herein, means the direction in which precursor webs are formed, which is the longitudinal direction of an uncut web.

The term "transverse direction", as used herein means the cross direction, disposed at 90° to the machine direction, and extends across the width of the initially formed precursor web.

Figure 1:
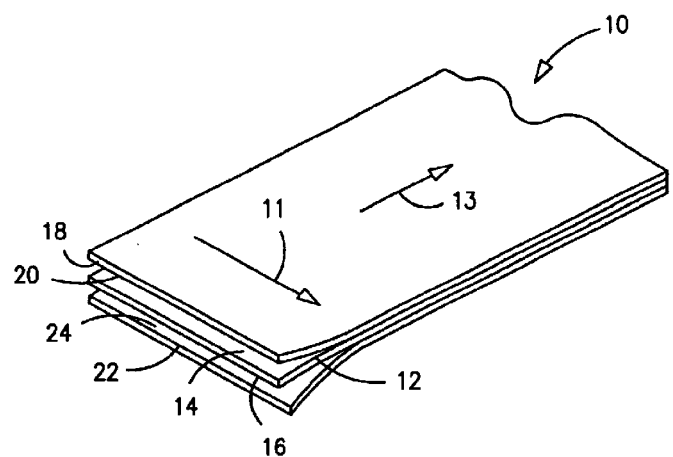
FIG. 1 is a three-dimensional view of a three-layer tear resistant laminate embodying the present invention.

A first preferred embodiment of a tear resistant laminate embodying the present invention is generally indicated by the reference numeral 10 in FIG. 1. The laminate 10 is suitable for use in sanitary products that require a closure system provided by the laminate 10 that is soft to the touch and can stretch in a transverse direction indicated by the arrow 11. The three-layer laminate 10 illustrated in FIG. 1 has a center ply that is formed of an elastic polymeric film 12 having a top surface 14 and a bottom surface 16. A top layer comprises a first nonwoven web 18 having a bottom surface 20 that is bonded to the top surface 14 of the elastomeric film 12. The bottom ply of the laminate 10 comprises a second nonwoven web 22 having a top surface 24 that is bonded to the bottom surface 16 of the elastomeric film 12.

The elastic polymeric film 12 may be formed of either a metallocene based low density polyethylene (m-LDPE), or a block-copolymer blend that contains styrene/butadiene/styrene (SBS), styrene/ethylene-butylene/styrene (SEBS), ethylene vinyl acetate (EVA), thermoplastic urethane, or cross-linked rubber. Desirably, the elastic polymeric film 12 has a basis weight of from about 18 g/m² to about 100 g/m². Preferably, an m-LDPE film has a basis weight of about 25 g/m², whereas block copolymer films have a basis weight of about 50 g/m². Also, it is desirable that the elastic polymeric files have less than 25% set when stretched 50%.

In addition to having good elasticity, it is also desirable that the elastic polymeric film 12 be puncture resistant. For example, if the laminate 10 embodying the present invention is used to form pull tabs, or ears, for diaper products, it is important that the laminate not be easily punctured by long fingernails. Since nonwoven materials generally provide little or no puncture resistance, the elastic polymeric film 12 should have a puncture resistance, as represented by a Dart Impact value, of at least 400 g.

In an exemplary embodiment, a low density polyethylene film (m-LDPE) having a basis weight of 25 g/m² was used as the middle layer 12 in a multiple layer laminate. The m-LDPE film was tested and found to have the elastic properties listed below in Table I.

TABLE I

MEASURED PROPERTIES OF ELASTOMERIC FILM

| | | |
|---|---|---|
| Thickness | 1 mil | (25 μm) |
| Tensile force in transverse direction (per unit of sample width): | | |
| at 25% elongation | 181 N/m | (468 g/in) |
| at 50% elongation | 205 N/m | (532 g/in) |
| at break | 611 N/m | (1583 g/in) |
| Elongation at break | | 588.5% |
| Dart impact | | 750 g |

The first and second nonwoven webs 18, 22 are formed of nonelastomeric thermoplastic fibers that have good, uniform but random, filament/fiber distribution. The fiber orientation should be such as to provide a degree of fiber randomization wherein at least some of the random fibers are disposed at an angle with respect to a machine direction of the web 13 that is equal to or greater than 10°. In the preferred embodiments of the present invention, the nonwoven webs 18, 22 are formed of spunbond nonwoven fibers which have a mass divided by length value of at least about 1.5 denier, and preferably from about 2.0 to about 3.5 denier per filament. The polymer composition of the fibers is desirably a polyolefin, and preferably polypropylene or polyethylene/polypropylene blends or other bicomponent blends having polypropylene as one component of the blend.

In an illustrative exemplary embodiment of the present invention, a spunbond thermoplastic polypropylene nonwoven fabric is used as a precursor web in forming the nonwoven webs 18, 22 of the laminate 10 embodying the present invention, produced by Avgol Nonwoven Industries, Ltd. of Holon, Israel and has the properties listed below in Table II.

TABLE II

MEASURED PROPERTIES OF PRECURSOR NONWOVEN WEB

| | | |
|---|---|---|
| Basis Weight | 25 g/m² | |
| Tensile force in transverse direction (per unit of width): | | |
| at 25% elongation | 539 N/m | (1396 g/in) |
| at 50% elongation | 785 N/m | (2033 g/in) |
| at break | 843 N/m | (2183 g/in) |
| Elongation at break | | 72.5% |
| fiber thickness (mass divided by length) | | 2.0 denier |

The initial nonwoven fabric, described above in Table II, was then consolidated laterally in accordance with the post-treatment processing of nonwoven webs described in U.S. Pat. Re. 35,206 reissued Apr. 16, 1996 to Charles B. Hassenboehler, Jr., et al. and titled POST-TREATMENT OF NONWOVEN WEBS. More specifically, in the illustrative embodiment, an initial precursor nonwoven web having a width of 1.37 m (54 in.) was laterally consolidated to a width of 0.84 m (33 in.), resulting in a neck-down ratio (ratio of original width to consolidated width) of about 1.6:1. In forming the first and second nonwoven webs 18, 20 embodying the present invention, it is generally desirable to consolidate the precursor webs by a factor of from at least about 1.3:1 to about 4:1 (original width to consolidated width). As described above, it is desirable that the thermoplastic fibers comprising each of the nonwoven webs are randomly disposed within the web, preferably skewed at an angle greater than about 10° from the machine direction 13. Preferably, at least about 2% and up to about 50% of the thermoplastic fibers are disposed in the skewed direction. Also, it is desirable that the basis weight of the precursor webs be in a range of from about 14 g/m² to about 60 g/m² (0.003 lb. per ft.² to 0.012 lb./ft.²).

Importantly, the first and second nonwoven webs 18, 22 have essential properties measured in the transverse direction 11, after consolidation. The consolidation should be sufficient to provide a nonelastic elongation range in the transverse direction of from about 20% to about 200%, and have an ultimate force to break of greater than 580 N/m (1500 g/in.). The nonwoven webs 18, 22 representing the illustrative example of a preferred embodiment of the present invention were consolidated as described above to a neck-down ratio of about 1.6:1. The consolidated nonwoven web was then tested and found to have the elongation properties listed below in Table III.

TABLE III

PROPERTIES OF CONSOLIDATED NONWOVEN WEB

| | | |
|---|---|---|
| Tensile force in transverse direction (per unit of sample width): | | |
| at 25% elongation | 29 N/m | (74 g/in) |
| at 50% elongation | 266 N/m | (690 g/in) |
| at break | 666 N/m | (1725 g/in) |
| Elongation at break | | 109.8% |

Figure 2:
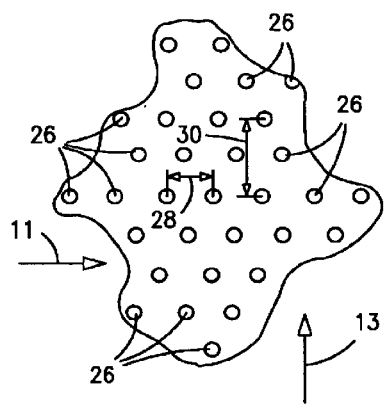
FIG. 2 is a plan view of a preferred weld bond pattern whereby the multiple layers of the tear resistant laminate embodying the present invention are bonded together.

After forming, the first and second nonwoven webs 18, 22 were bonded to the elastomeric film 12. More specifically, as shown in FIG. 1, the bottom surface 20 of the first nonwoven web 18 is bonded to the top surface 14 of the film 12, and the top surface 24 of the second nonwoven web 22 is bonded to the bottom surface 16 of the elastomeric film 12. Preferably, the bonding between the respective webs 18, 22 and elastomeric film 12 is carried out simultaneously by the use of ultrasonic or fusion bonding. For this purpose, it is desirable that at least about 10% of the randomly disposed fibers in the first and second webs 18, 22 have approximately equal softening temperatures. The nonwoven webs 18, 22 are thus welded, preferably by a combination of thermal and mechanical energy, to provide a peel force greater than 155 N/m (400 g/in.) of width. To provide the adequate peel force, it has been found that a weld area of at least 3.0% of the total contiguous surface area at each of the layer interfaces should participate in the bonding. A pattern of ⅛ mm diameter weld areas, arranged in a geometric pattern as illustrated in FIG. 2, is sufficient to provide the required mutual bonding area. With continued reference to FIG. 2, the spacing 28 of the ⅛ mm diameter common bond areas 26 in the transverse direction 11, in the illustrative example, is 4 mm. The spacing 30 between the ⅛ mm diameter common bond areas 26 in the machine direction 13, of the illustrative example, is 7 mm. As illustrated in FIG. 2, the ⅛ mm common bond areas 26 are arranged to form a series of open trapezoidal figures using a "zig-zag" pattern. The spaced apart point bonds provided by the arrangement illustrated in FIG. 2 assures that all layers, 12, 18, 22 of the laminate 10 are adequately connected and that any force exerted on any one of the layers 12, 18, 22, or on the laminate 10 as a whole, is distributed through all of the layers 18, 12, 22. This arrangement is markedly different than adhesive bonding or extrusion lamination which join only two adjacently disposed layers.

Figure 3:
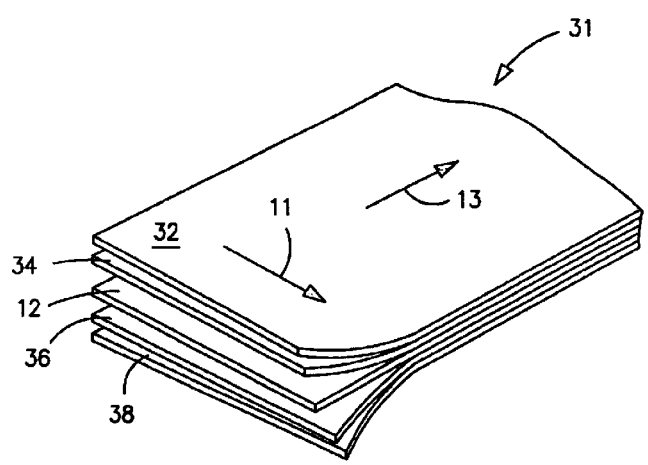
FIG. 3 is a three-dimensional view of a five-layer tear resistant laminate embodying the present invention.

A second exemplary embodiment of the present invention is illustrated in FIG. 3. In this embodiment, a five-layer laminate 31 comprises two external layers of nonwoven web on each side of the centrally disposed elastomeric film 12. More specifically, a first nonwoven web 32 and a second nonwoven web 34 are bonded to each other and to the elastomeric film 12 on the upper side of the film 12, and a third nonwoven web 36 and a fourth nonwoven web 38 are bonded to each other and to the bottom surface of the elastomeric film 12. The two double plies of nonwoven web, 32, 34, and 36, 38 strengthen the laminate 31 while maintaining a soft external surface of the laminate 31. In this embodiment, as well as in the earlier described embodiment of the three-layer laminate 10, it is necessary that at least a portion of the fibers comprising each of the nonwoven webs have a similar softening temperature. In forming the five-layer laminate 31, all of the plies, i.e., the first nonwoven web 32, the second nonwoven web 34, the elastomeric film 12, the third nonwoven web 36 and the fourth nonwoven web 38, may be bonded simultaneously by ultrasonic welding or other point fusion welding methods. Alternatively, if so desired, the first and second nonwoven webs 32, 34 may be prebonded to each other to form a single structure, and the third and fourth nonwoven webs 36, 38 may be prebonded to each other to form a second structure, prior to bonding the thus formed double nonwoven web structures to the elastomeric film 12. Also, if so desired, the elastomeric film 12 may comprise two or more layers of film having similar, or even different, elasticity properties to provide greater tear resistance and minimize the possibility of catastrophic failure. In this arrangement, the nonwoven webs are respectively bonded to the top and bottom surfaces of the assembled multi-layered elastomeric film 12.

Figure 4:
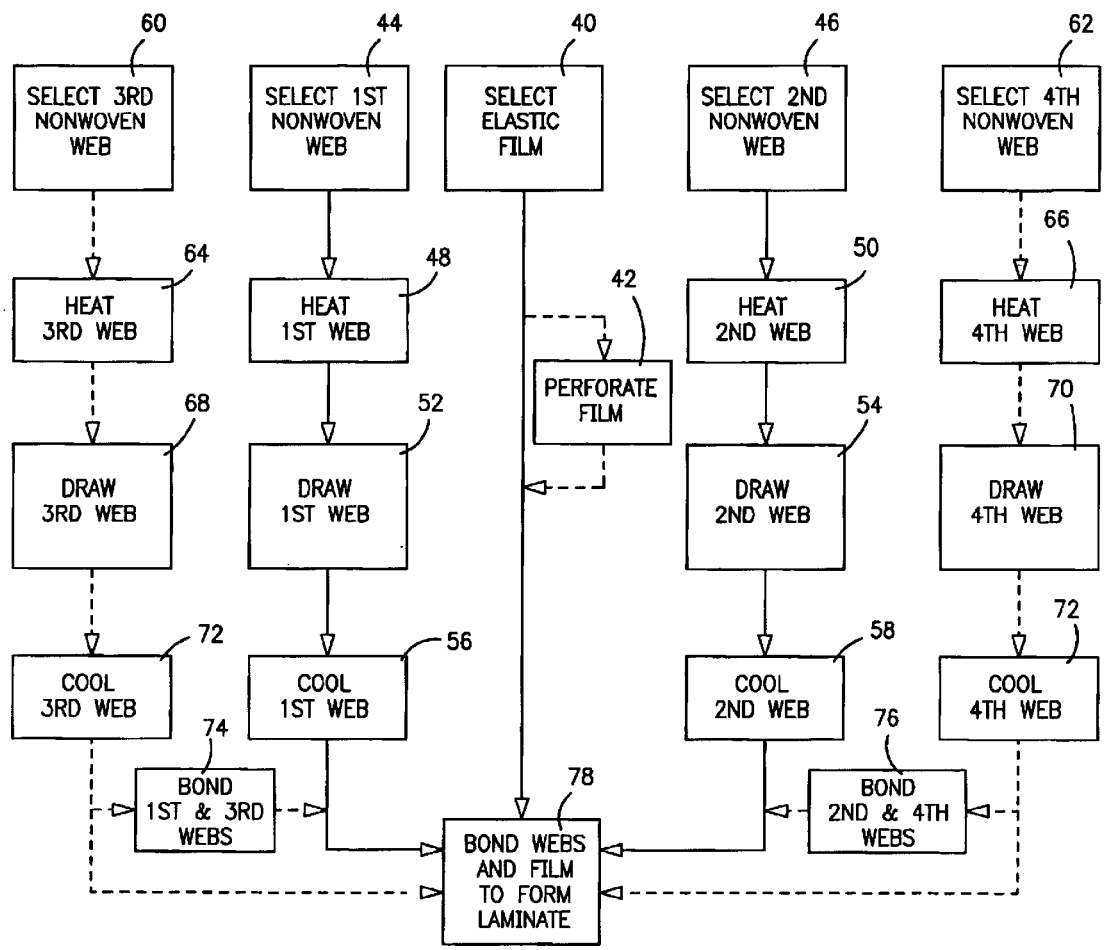
FIG. 4 is a flow diagram of a method for forming the tear resistant laminate in accordance with the present invention.

In accordance with another aspect of the present invention, a method for forming a tear resistant laminate is carried out in accordance with the steps outlined in FIG. 4. The steps include selecting an elastomeric polymeric film 12 having a basis weight of from about 18 g/m² to about 100 g/m², as represented by block 40. As noted above, the elastomeric film 12 may comprise multiple layers, if so desired. In the preferred embodiment, the elastic polymeric film 12 is a metallocene based low density polyethylene having a basis weight of from about 18 g/m² to about 25 g/m². If it is desired to form a breathable web, the elastomeric film 12 may be perforated, such as by hot needle perforation or vacuum perforation, as indicated by block 42.

First and second precursor nonwoven webs having the properties described above are then selected as represented by blocks 44 and 46. The first and second precursor webs are then heated to a temperature between the softening temperature and the melting temperature of the thermoplastic fibers comprising the webs, as indicated at blocks 48 and 50. The heated webs are then drawn in the machine direction, under tension, to cause the web to be elongated in the machine direction and consolidated laterally in the transverse direction as represented by blocks 52 and 54 in FIG. 4. The first and second webs are then cooled whereby the nonwoven webs 18, 22 are consolidated laterally and have an original precursor width to consolidated width ratio of from about 1.3:1 to about 4:1. The cooling steps for the first and second webs are indicated by blocks 56, 58. The consolidation process for the first and second webs, represented by blocks 44–58 of FIG. 4, are carried out in accordance with the consolidation process described in the above-referenced U.S. Pat. Re. 35,206, with the exception of heat setting the drawn webs.

If, in the above-described alternative exemplary embodiment, the five-layer laminate 31 is formed, the third and fourth nonwoven webs are selected, heated, drawn, and cooled as described above with reference to the first and second nonwoven webs, and as represented by blocks 60–72 of FIG. 4. If desired, the first and third nonwoven webs 18, 36, and the second and fourth webs, 22, 38, may be bonded to each other as represented at blocks 74 and 76 prior to final assembly of the laminate 31. Alternatively, the first, second, third and fourth nonwoven webs 18, 22, 36, 38 may all be simultaneously bonded to the elastomeric film 12.

The consolidated webs, 18–22, and if so desired in the alternate embodiment, the additional nonwoven webs, are bonded, as described above, to form a single laminate structure 10, 31, having an elastic elongation range of up to 200% and an ultimate force to break of greater than 772 N/m (2000 g/in.). The multiple layers of the laminate are joined together by fusion bonds that have a collective area of at least 3.0% of the total contiguous surface area of adjacently disposed layers and a peel strength per unit width of greater than 154 N/m (400 g/in.). If the elastomeric film 12 is a multi-layered film, all layers of the elastomeric film structure may be simultaneously bonded together during bonding of the laminate structure.

More specifically, the measured elongation characteristics of the exemplary embodiment described above having the elastomeric film 12 and two nonwoven webs 18, 22, one bonded on each side of the elastomeric film 12, are listed in Table IV. A two-inch wide sample of the laminate 10, was assembled in accordance with the above described method and tested using a 3-inch jaw gap and a 20-inch/minute crosshead speed.

TABLE IV

MEASURED PROPERTIES OF THREE-LAYER LAMINATE

Tensile force in transverse direction
(per unit of width):

| | | |
|---|---|---|
| at 25% elongation | 240 N/m | (621 g/in.) |
| at 50% elongation | 513 N/m | (1328 g/in.) |
| at break | 1575 N/m | (4080 g/in.) |
| Elongation at break | | 135.6% |

In addition to the measured elongation properties listed above in Table IV, an additional sample was slit ½ inch deep across the sample width and then stretched in an attempt to induce a tear. The sample failed before a tear across the width of the sample was initiated. This test clearly demonstrated the excellent tear resistance of the laminate 10, 31 embodying the present invention.

INDUSTRIAL APPLICABILITY

The laminate 10, 31 provided by the present invention provides a lightweight, cloth-like, film-based laminate that has an elastic recovery from stretching that is comparable to natural or synthetic rubber films in the transverse direction and has a tear-resistance that is comparable to durable cotton or a stitched LYRCA® material. The laminate 10, 31 provided by the present invention is particularly useful for use as an elastic diaper ear that can be stretched to accommodate the different anatomies of variously sized wearers, and simultaneously improve the fit and reduce leakage around the perimeter of the diaper as a result of the better fit. The laminate provided by the present invention is also useful for use in other sanitary product applications that require a closure system that is lightweight, has good elasticity, is tear-resistant, and is soft to the touch. If a breathable tear-resistant laminate is desired, the layer of elastomeric film 12, encapsulated between at least two layers of nonwoven web, may be perforated.

Although the present invention is described in terms of preferred exemplary embodiments, with specific measured values of illustrative components, those skilled in the art will recognize that changes in those components which may result in different measured values, but still be in accordance with the teachings of the present invention, may be made without departing from the spirit of the invention. Such changes are intended to fall within the scope of the following claims. Other aspects, features, and advantages of the present invention may be obtained from a study of this disclosure and the drawings, along with the appended claims.

What is claimed is:

1. A method for forming a finished product incorporating a tear resistant laminate, comprising:
   (a) selecting an elastic polymeric film having a basis weight of from about 18 g/m2 to about 100 g/m2;

(b) selecting a first precursor nonwoven web formed of randomly disposed nonelastomeric thermoplastic fibers and having predefined machine and transverse directions, wherein the first precursor nonwoven web is selected so that at least 10% of the fibers of the first precursor nonwoven web have a softening temperature approximately equal to a predetermined softening temperature;

(c) heating the first precursor nonwoven web to a temperature between the predetermined softening temperature and the melting temperature of any of the fibers of the first precursor nonwoven web;

(d) drawing the heated first precursor nonwoven web under tension in said predefined machine direction to cause the first precursor nonwoven web to be longitudinally elongated in said machine direction and consolidated laterally in said predefined transverse direction, thereby forming a first nonwoven web;

(e) cooling the first nonwoven web whereby the first nonwoven web is consolidated in said transverse direction, and has an extensible elongation value in said transverse direction of from about 20% to about 200% and an ultimate force to break in said transverse direction of greater than about 1500 g/in.;

(f) selecting a second precursor nonwoven web formed of randomly disposed nonelastomeric thermoplastic fibers and having predefined machine and transverse directions, wherein the second precursor nonwoven web is selected so that at least 10% of the fibers of the second precursor nonwoven web have a softening temperature approximately equal to the predetermined softening temperature;

(g) heating the second precursor nonwoven web to a temperature between the predetermined softening temperature and the melting temperature of any of the fibers of the nonwoven web;

(h) drawing the heated second precursor nonwoven web under tension in said predefined machine direction to cause the second precursor nonwoven web to be longitudinally elongated in said machine direction and consolidated laterally in said predefined transverse direction, thereby forming a second nonwoven web;

(i) cooling the second nonwoven web whereby said second nonwoven web is consolidated in said transverse direction, and has an extensible elongation value in said transverse direction of from about 20% to about 200% and an ultimate force to break in said transverse direction of greater than about 1500 g/in.;

(j) bonding a bottom surface of the first nonwoven web to a top surface of the elastic polymeric film and simultaneously bonding a top surface of the second nonwoven web to a bottom surface of the elastic polymeric film to produce a tear resistant laminate; and (k) incorporating the tear-resistant laminate into a finished product without further substantial necking of the laminate.

2. The method set forth in claim 1, where said bonding a bottom surface of the first nonwoven web to the top surface of the elastic polymeric film and simultaneously bonding the top surface of the second nonwoven web to the bottom surface of the elastic polymeric film includes bonding the respective webs and the elastic polymeric film together by thermal fusion with the addition of an applied pressure to produce mutually bonded surface areas between the respective adjacently disposed web and film surfaces comprising at least about 3.0% of the total adjacently disposed surface areas.

3. The method set forth in claim 1, wherein said bonding a bottom surface of the first nonwoven web to the top surface of the elastic polymeric film and simultaneously bonding the top surface of the second nonwoven web to the bottom surface of elastic polymeric film includes ultrasonically heating spaced-apart preselected portions of the webs and film to produce mutually bonded surface areas between the respective adjacently disposed web and film surfaces of at least 3.0% of the total adjacently disposed surface areas.

4. The method set forth in claim 1, wherein said selecting an elastic polymeric film includes perforating the elastic polymeric film prior to bonding with the bottom surface of the first nonwoven web and the top surface of the second nonwoven web.

5. The method set forth in claim 1, wherein said method includes selecting at least one precursor nonwoven web formed of randomly disposed nonelastomeric thermoplastic fibers, heating the at least one precursor web to a temperature between the softening temperature and the melting temperature of at least 10% of the fibers comprising the additional nonwoven web, drawing the heated at least one additional web whereby the additional web is elongated longitudinally and consolidated laterally, cooling the at least one additional web thereby forming an additional nonwoven web having a defined elastic elongation value and an ultimate force to break value in the transverse direction substantially equal to said elastic elongation value and ultimate force to break value in the transverse direction of said first and second nonwoven webs, and bonding said at least one additional nonwoven web to one of said first and second webs.

6. The method set forth in claim 5, wherein said bonding said at least one additional nonwoven web to one of said first and second webs is carried out prior to bonding a bottom surface of the first nonwoven web to the top surface of the elastic polymeric film and simultaneously bonding the top surface of the second nonwoven web to the bottom surface of the elastic polymeric film.

7. The method set forth in claim 1, wherein said selecting an elastic polymeric film includes selecting an elastic polymeric film comprised of multiple layers of elastic polymeric film.

* * * * *